United States Patent
Kim et al.

(10) Patent No.: US 12,111,316 B2
(45) Date of Patent: Oct. 8, 2024

(54) REFERENCE CASSETTE FOR FLUORESCENCE IMMUNOASSAY DIAGNOSTIC DEVICE

(71) Applicant: PRECISION BIOSENSOR INC., Daejeon (KR)

(72) Inventors: Hee Jun Kim, Daejeon (KR); Sung Joon Kim, Daejeon (KR)

(73) Assignee: PRECISION BIOSENSOR INC., Daejeon (KR)

( * ) Notice: Subject to any disclaimer, the term of this patent is extended or adjusted under 35 U.S.C. 154(b) by 653 days.

(21) Appl. No.: 17/418,817

(22) PCT Filed: Dec. 10, 2019

(86) PCT No.: PCT/KR2019/017352
§ 371 (c)(1),
(2) Date: Jun. 27, 2021

(87) PCT Pub. No.: WO2020/138764
PCT Pub. Date: Jul. 2, 2020

(65) Prior Publication Data
US 2022/0074933 A1     Mar. 10, 2022

(30) Foreign Application Priority Data
Dec. 28, 2018   (KR) .................. 10-2018-0172630

(51) Int. Cl.
*G01N 33/543*     (2006.01)
*G01N 21/64*      (2006.01)
(Continued)

(52) U.S. Cl.
CPC ... *G01N 33/54388* (2021.08); *G01N 21/6447* (2013.01); *G01N 21/645* (2013.01);
(Continued)

(58) Field of Classification Search
CPC ....... G01N 33/54388; G01N 33/54386; G01N 33/558; G01N 21/645; G01N 21/6447;
(Continued)

(56) References Cited

U.S. PATENT DOCUMENTS

2019/0187058 A1*  6/2019  Hasegawa .......... G01N 21/6489
2019/0310270 A1* 10/2019  Hyun ...................... G01N 33/92

FOREIGN PATENT DOCUMENTS

JP   2007-538230   12/2007
JP   2013-146263    8/2013
(Continued)

OTHER PUBLICATIONS

International Search Report for PCT/KR2019/017352 mailed on May 15, 2020 and its English translation from WIPO (now published as WO 2020/138764).
(Continued)

*Primary Examiner* — Jennifer Wecker
*Assistant Examiner* — Kathryn Elizabeth Limbaugh
(74) *Attorney, Agent, or Firm* — Ladas & Parry, LLP (57) ABSTRACT

Provided in the present invention is a reference cassette for a fluorescence immunoassay diagnostic device, the cassette having, arranged in a case, fluorescent glass capable of maintaining fluorescence characteristics to be constant without causing degeneration, so as to accurately provide reference measurement information about the fluorescence detection amount during testing of the measurement accuracy of the fluorescence detection of the immunoassay diagnostic device, so that testing accuracy can improve, preventing decrease in measurement accuracy and being semi-permanently usable since the denaturation or deterioration of the fluorescent glass does not occur even if the cassette is used continuously, and providing a mask having a slit so as to limit the area of the fluorescent glass to be externally
(Continued)

exposed to a specific area, thereby generating the type of fluorescence that is the same as that of a reaction area of a sample strip to be actually used, and thus more accurate reference measurement information can be provided.

3 Claims, 4 Drawing Sheets

(51) Int. Cl.
*G01N 21/77* (2006.01)
*G01N 21/84* (2006.01)
(52) U.S. Cl.
CPC . *G01N 21/8483* (2013.01); *G01N 2021/6482* (2013.01); *G01N 2021/7759* (2013.01); *G01N 2021/7786* (2013.01)

(58) Field of Classification Search
CPC ....... G01N 21/8483; G01N 2021/6482; G01N 2021/7759; G01N 2021/7786
See application file for complete search history.

(56) References Cited

FOREIGN PATENT DOCUMENTS

| KR | 10-2015-0031007 | 3/2015 |
| KR | 10-1661986 | 10/2016 |
| KR | 10-2018-0072098 | 6/2018 |

OTHER PUBLICATIONS

Written Opinion of the International Searching Authority for PCT/KR2019/017352 mailed on May 15, 2020 and its English translation by Google Translate (now published as WO 2020/138764).

* cited by examiner

REFERENCE CASSETTE FOR FLUORESCENCE IMMUNOASSAY DIAGNOSTIC DEVICE

CROSS-REFERENCE TO RELATED APPLICATIONS

This application is the U.S. National Stage of International Patent Application No. PCT/KR2019/017352 filed on Dec. 10, 2019, which claims the priority to Korean Patent Application No. 10-2018-0172630 filed in the Korean Intellectual Property Office on Dec. 28, 2018, the entire contents of which are incorporated herein by reference.

TECHNICAL FIELD

The present disclosure is generally related to a reference cassette for a fluorescence type immunoassay diagnostic apparatus. More specifically, the present disclosure is related to a reference cassette for a fluorescence type immunoassay diagnostic apparatus in which, by arranging fluorescence glass, which does not change in characteristics and is capable of constantly maintaining fluorescence characteristics, inside a case, in a process of testing measurement accuracy regarding fluorescence detection of the immunoassay diagnostic apparatus, reference measurement information regarding the fluorescence detection can be precisely provided and therefore the accuracy of the test can be improved, because the change in characteristics and heat deterioration of the fluorescence glass do not occur, the measurement accuracy may not be lowered even it is continuously used and it can be used semi-permanently, and by having a mask at which slits limiting an outside exposure area of the fluorescence glass to a specific area are formed, the fluorescence having the same shape as the reaction area of the actually used specimen strip can be generated.

BACKGROUND

Generally, a test method used in disease diagnosis is based on color development, fluorescence and so on by enzyme reaction, but recently immunoassay using immunization reaction between an antigen and an antibody is also being used. Such immunoassay methods mainly label antibodies with radioisotopes or fluorescent substances to identify the presence or absence of antigens, and label type biosensors are used to quantify the intensity of radiation or fluorescence.

Conventional immunoassay methods have used a method of measuring a signal obtained by labeling antigens or antibodies with radioactive substances, luminescent substances or fluorescent substances, and optical measurement methods such as Enzyme Linked Immunosorbent Assays (ELISAs) combining photolabels with catalytic reactions of enzymes and Western blotting. Those methods have disadvantages in that complex procedures that can be performed primarily by laboratory-based skilled researchers are required, the devices for analysis are expensive and large-scale devices, and long analysis time is needed.

Because antibodies, which are the target substance of an immune sensor, are present in very low concentrations in biological samples such as whole blood, serum, urine and so on, the immune sensor requires to have a signaling technology which is much more highly sensitive than the biosensor technology of detecting other substances in terms of detection limit of the sensor. In addition, since the structure of protein such as antibodies or protein antigens are easily altered by changes in the external environment, the recognition portion of the antigen or antibody is deteriorated, and thus unique biometric recognition function is easily lost. Because the immune sensor requires to perform analysis in the solid form, the production of a sensor surface suitable for the biopsy materials that can maintain the activation of the biopsy materials, the immobilization technology of the biopsy materials which can increase the detection limit, and the measurement method transforming biometric recognition reaction to quantified signals are needed.

Rapid diagnostic test kits for immunoassay are test instruments for point-of-care that is capable of performing diagnostic test using biopsy specimens such as blood, urine, and saliva. Examples of such rapid diagnostic test kits include pregnancy diagnosis kits, AIDS diagnosis kits, and so on.

Those diagnostic devices require to establish a method capable of detecting biomaterial (protein or DNA, etc.) for diagnosis. A fluorescent labeling method using an organic dye or the like has been known as a conventional method for detecting the biomaterial. The fluorescent label emits various colors depending on types to provide a detection means for a target biomaterial.

The immunoassay diagnostic devices use a specimen strip capable of absorbing and supplying biopsy specimen through capillary phenomenon, and a plurality of reaction areas are formed at the specimen strip by applying different reaction material to each of the reaction areas. In the plurality of reaction regions, each reactive substance is combined with a biopsy specimen having a specific disease to form a fluorescent reaction complex, and the fluorescent reaction complex generates fluorescence when light is applied. Accordingly, after inserting the specimen strip into the device, the test light is applied to the specimen strip from a light source, and fluorescence generated from the reaction region of the specimen strip is detected by an optical system, thereby diagnosing a specific disease associated with the biopsy specimen.

As those types of the immunoassay diagnostic devices are used for a long time, the measurement accuracy may be deteriorated due to an abnormality in the optical system or other control unit, and a measurement error may occur because of the change in the characteristics of the reaction material applied to the specimen strip. Therefore, it is necessary for the immunoassay diagnosis devices using a fluorescent type specimen strip to periodically check whether the measurement accuracy of the immunoassay diagnosis device is accurate.

In order to test the measurement accuracy of the immunoassay diagnostic device, a separate reference cassette is used, and the reference cassette is manufactured in a state that a test strip is accommodated therein and a fluorescent substance in an unmodified standard state is applied to the test strip. The reference cassette is inserted into the device to apply test light, and fluorescence generated from the fluorescent material of the test strip is detected to check whether a measurement error occurs in the device. That is, if the detection amount of the fluorescence detected by inserting the reference cassette into the device is different from a predetermined standard detection amount, an error occurs in the device, and an error occurrence alarm sign may be output through a display unit of the device.

Accordingly, the reference cassette for testing the measurement accuracy of the immunoassay diagnostic device requires to be manufactured very precisely, and the fluorescent material applied to the test strip of the reference cassette also needs to be maintained constantly in a standard state in which the characteristics are not changed. However, the fluorescent substance is easily denatured by the external environment due to its characteristics and therefore it is difficult to maintain the characteristics of the standard state, and in this case, the reference cassette cannot perform normal function as the reference cassette for testing the measurement accuracy of the immunoassay diagnostic device.

Therefore, in order to precisely check the measurement accuracy of the immunoassay diagnostic device, stably maintaining the standard state of the reference cassette is highly important, and recently the demand and necessity thereof are increasing.

DETAILED DESCRIPTION OF DISCLOSURE

Technical Problem

To solve the problem of the conventional art, the purpose of the present disclosure may be for providing a reference cassette for a fluorescence type immunoassay diagnostic apparatus in which, by arranging fluorescence glass, which does not change in characteristics and is capable of constantly maintaining fluorescence characteristics, inside a case, in a process of testing measurement accuracy regarding fluorescence detection of the immunoassay diagnostic apparatus, reference measurement information regarding the fluorescence detection can be precisely provided and therefore the accuracy of the test can be improved, because the change in characteristics and heat deterioration of the fluorescence glass do not occur, the measurement accuracy may not be lowered even it is continuously used and it can be used semi-permanently.

Another purpose of the present disclosure may be for providing a reference cassette for a fluorescence type immunoassay diagnostic apparatus in which, by having a mask at which slits limiting an outside exposure area of the fluorescence glass to a specific area are formed, the fluorescence having the same shape as the reaction area of the actually used specimen strip can be generated and therefore more accurate reference measurement information can be provided.

Still another purpose of the present disclosure may be for providing a reference cassette for a fluorescence type immunoassay diagnostic apparatus in which by guiding the coupling location of the fluorescence glass and the mask, the position of the fluorescence glass and the mask can be precisely maintained and accordingly the test accuracy can be improved.

Still another purpose of the present disclosure may be for providing a reference cassette for a fluorescence type immunoassay diagnostic apparatus in which a mask is formed in a metal plate shape and is arranged to contact the upper surface of fluorescence glass and therefore during a process that test light and fluorescence pass through the slit of the mask the influence of the shadow can be minimized and the fluorescence measurement accuracy can be improved.

Solution to Problem

According to various embodiments of the present disclosure, a reference cassette for a fluorescence immunoassay diagnostic apparatus which is inserted into the apparatus diagnosing a disease from a biopsy specimen using fluorescence and generates fluorescence by a test light of an optical module, the reference cassette for the fluorescence immunoassay diagnostic apparatus may comprise: a case configured to be insertable into the fluorescence immunoassay diagnostic apparatus, wherein an opening is formed at at least a part of an upper side of the case so that an inner space of the case is exposed to an outside of the case; and a fluorescence glass disposed at the inner space of the case so that the fluorescence glass is exposed to the outside of the case through the opening of the case, wherein the fluorescence glass is configured to generate the fluorescence by the test light of the optical module and constantly maintain fluorescence characteristics.

In this embodiment, a mask may be disposed on an upper surface of the fluorescence glass inside the case so that an area of the fluorescence glass exposed to the outside of the case can be limited to a specific area of the fluorescence glass.

Additionally, the mask may have one or more slits, the fluorescence glass is exposed through the slits, the test light of the optical module may be applied to the fluorescence glass through the slits, and the fluorescence generated by the fluorescence glass is emitted to the optical module through the slits.

Further, a separate fixing guide having a plurality of insertion coupling holes may be coupled to an inside of the case, the fluorescence glass may include a plurality of pieces of the fluorescence glass, each piece of the fluorescence glass may be insertedly coupled to a respective insertion coupling hole of the fixing guide, and the mask may be coupled to the fixing guide so that each of the slits can limit an outside exposure area of the fluorescence glass to a slit area.

In addition, a guide protrusion may be formed at the fixing guide to guide a coupling location of the mask, and a guide hole may be formed at the mask to be insertedly coupled with the guide protrusion.

Additionally, an upper surface of the fluorescence glass and an upper surface of the fixing guide may be in a same plane as each other in a state that the fluorescence glass is insertedly coupled to the insertion coupling holes of the fixing guide, and the mask may be coupled to the fixing guide to contact the upper surface of the fluorescence glass and the upper surface of the fixing guide.

Further, the slits of the mask and the fluorescence glass may cross the opening of the case in one direction in a state that the slits of the mask and the fluorescence glass are arranged inside the case by the fixing guide.

Advantageous Effects of Invention

An embodiment of the present disclosure has advantageous technical effect in which, by arranging fluorescence glass, which does not change in characteristics and is capable of constantly maintaining fluorescence characteristics, inside a case, in a process of testing measurement accuracy regarding fluorescence detection of a immunoassay diagnostic apparatus, reference measurement information regarding the fluorescence detection can be precisely provided and therefore the accuracy of the test can be improved, and because the change in characteristics and heat deterioration of the fluorescence glass do not occur, the measurement accuracy may not be lowered even it is continuously used and it can be used semi-permanently.

Additionally, there may be advantageous technical effect in which, by having a mask at which slits limiting an outside exposure area of the fluorescence glass to a specific area are formed, the fluorescence having the same shape as the reaction area of the actually used specimen strip can be generated and therefore more accurate reference measurement information can be provided.

In addition, there may be advantageous technical effect in which, by guiding the coupling location of the fluorescence glass and the mask, the position of the fluorescence glass and the mask can be precisely maintained and accordingly the test accuracy can be improved.

Further, there may be advantageous technical effect in which, in which a mask is formed in a metal plate shape and is arranged to contact the upper surface of fluorescence glass and therefore during a process that test light and fluorescence pass through the slit of the mask the influence of the shadow can be minimized and the fluorescence measurement accuracy can be improved.

DESCRIPTION OF EMBODIMENTS OF DISCLOSURE

Hereinafter, preferred embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known components and functions incorporated herein will be omitted in the case that the subject matter of the present disclosure may be rendered unclear thereby.

Figure 1:
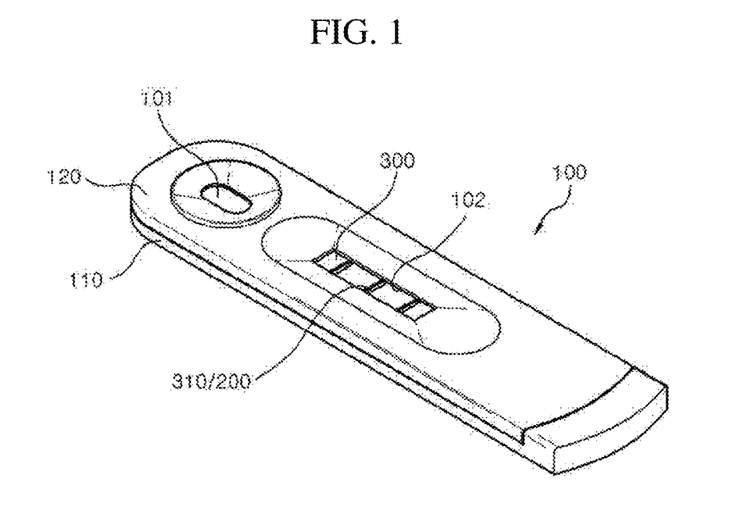
FIG. 1 is a perspective view schematically illustrating an outward appearance of a reference cassette for a fluorescence type immunoassay diagnostic apparatus according to an exemplary embodiment of the present disclosure.
Figure 2:
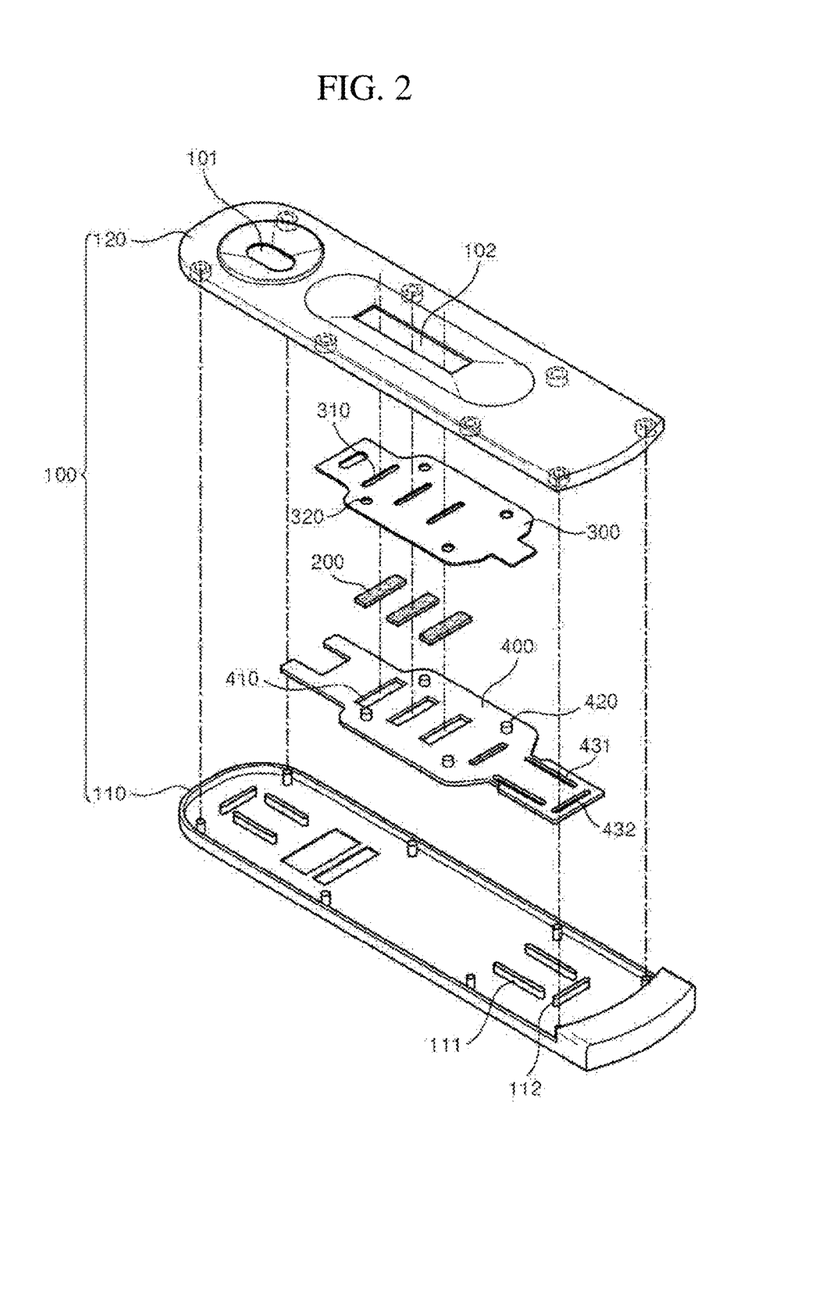
FIG. 2 is an exploded perspective view schematically illustrating specific configuration of a reference cassette for a fluorescence type immunoassay diagnostic apparatus according to an exemplary embodiment of the present disclosure.
Figure 3:
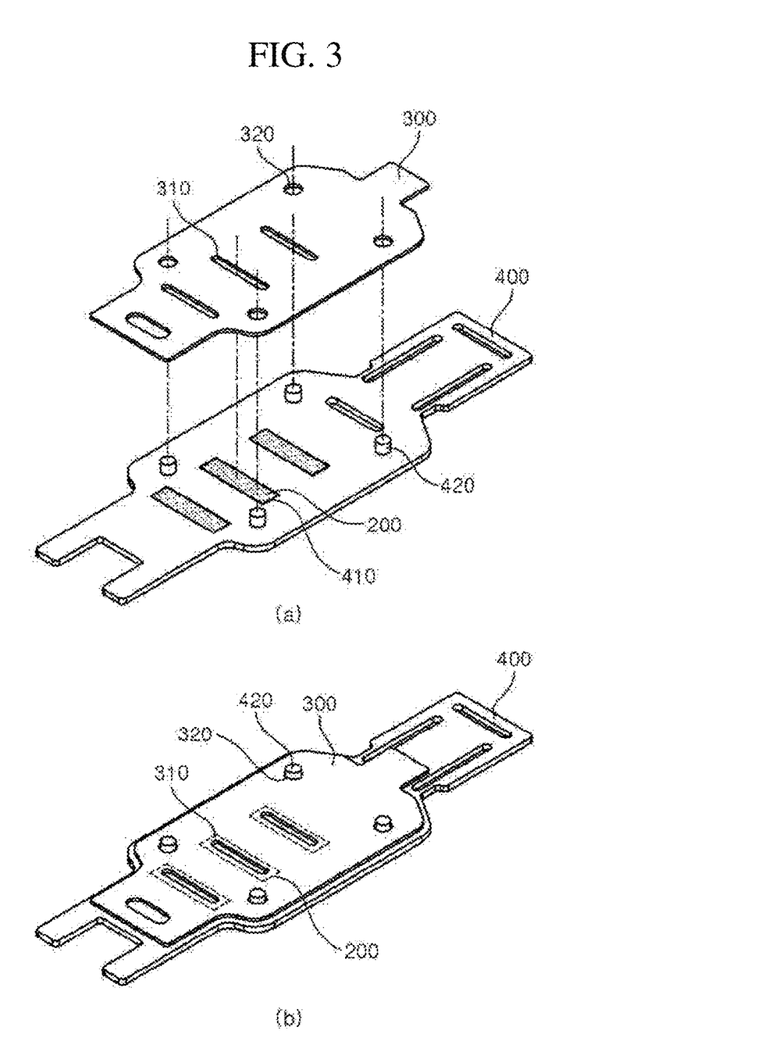
FIG. 3 is a view schematically illustrating a mask coupling arrangement structure of a reference cassette for a fluorescence type immunoassay diagnostic apparatus according to an exemplary embodiment of the present disclosure.
Figure 4:
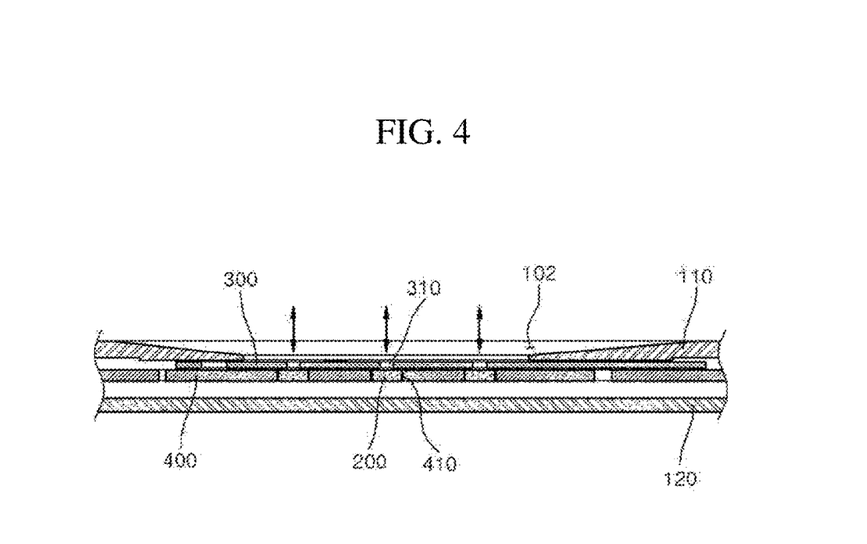
FIG. 4 is a cross-sectional view schematically illustrating an inner structure of a reference cassette for a fluorescence type immunoassay diagnostic apparatus according to an exemplary embodiment of the present disclosure.

FIG. 1 is a perspective view schematically illustrating an outward appearance of a reference cassette for a fluorescence type immunoassay diagnostic apparatus according to an exemplary embodiment of the present disclosure, FIG. 2 is an exploded perspective view schematically illustrating specific configuration of a reference cassette for a fluorescence type immunoassay diagnostic apparatus according to an exemplary embodiment of the present disclosure, FIG. 3 is a view schematically illustrating a mask coupling arrangement structure of a reference cassette for a fluorescence type immunoassay diagnostic apparatus according to an exemplary embodiment of the present disclosure, and FIG. 4 is a cross-sectional view schematically illustrating an inner structure of a reference cassette for a fluorescence type immunoassay diagnostic apparatus according to an exemplary embodiment of the present disclosure.

A reference cassette for a fluorescence type immunoassay diagnostic apparatus according to an exemplary embodiment of the present disclosure may be for being inserted into an immunoassay diagnostic apparatus in order to test measurement accuracy of the immunoassay diagnostic apparatus diagnosing a disease from a biopsy specimen using fluorescence and generating fluorescence by a test light of an optical module, may comprise a case (100), and a fluorescence glass (200), and may further include a mask (300) and a fixing guide (400).

The case (100) is configured to be insertable into the immunoassay diagnostic apparatus, and is formed to have an accommodating space to accommodating components such as the fluorescence glass (200) and so on. An opening unit (102) is formed at a partial area of an upper surface of the case (100) so that an inner space of the case (100) can be exposed, and the opening unit (102) can be protected by a separate transparent cover.

The case (100) may be formed to have an accommodating space therein, and include an upper case (120) and a lower case (110) which are separately formed and can be formed to have a structure coupled to each other. The lower case (110) forms a base of the case (100) and components are coupled to an inner side surface of the lower case (110), and in this state, the upper case (120) is coupled to an upside of the lower case (110). The opening unit (102) is formed at a center portion of an upper surface of the upper case (120), and a body fluid injection hole (101) is formed at one side of the upper surface of the upper case (120) so that body fluid specimen can be absorbably injected into the body fluid injection hole (101). The reference cassette may not need the body fluid injection hole (101), but the body fluid injection hole (101) may be included in the reference cassette to have an identical structure to an actual cassette.

A single sheet or a plurality of sheets of fluorescence glass (200) may be disposed in the inner space of the case (100) to be exposed to the outside of the case (100) through the opening unit (102) of the case (100). The fluorescence glass (200) may be made of lanthanide series material, and be configured to generate fluorescence by the test light of the optical module and constantly maintain fluorescence characteristics. Europium, terbium and so on can be used as the lanthanide series material.

Because the fluorescence characteristics of the fluorescence glass (200) is constantly maintained, the change does not occur in the characteristics, and therefore, in the process of testing measurement accuracy regarding fluorescence detection of the immunoassay diagnostic apparatus, the accuracy of the test may be improved.

The reference cassette comprising the fluorescence glass (200) does not have the change in the characteristics of the fluorescence glass (200) or heat deterioration and therefore the measurement accuracy may not be lowered even it is continuously used and there is advantage that it can be used semi-permanently.

If an extensive area of the fluorescence glass (200) is exposed to the outside of the case (100) through the opening unit (102) of the case (100), the fluorescence detection at a specific area by the optical module may not be easy and be inaccurate, and therefore a separate mask (300) that can limit an outside exposure area of the fluorescence glass (200) to a specific area may be installed.

The mask (300) is arranged at the inside of the case (100) to be located on an upper surface of the fluorescence glass (200). A plurality of slits (310) are formed at the mask (300), and the fluorescence glass (200) is configured to be exposed to the outside of the case (100) through the slits (310) of the mask (300).

Generally, in the immunoassay diagnostic apparatus, the reaction area of a specimen strip to which fluorescence is applied is formed in a line shape crossing the specimen strip, the slit (310) may be lengthily formed to extend in one direction and have a shape similar to the reaction area of the specimen strip, and the fluorescence glass (200) is outwardly exposed through the slit (310) with the line shape.

In this case, the test light of the optical module is applied to the fluorescence glass (200) through the slit (310), and the fluorescence generated from the fluorescence glass (200) by the application of the lest light is configured to be emitted to the optical module through the slit (310).

The mask (300) is made of material which is capable of blocking the light, and is formed in a shape of a thin plate having thin thickness to minimize shadow generated when the test light and the fluorescence pass through the slit (310). In this example, the material with high stiffness, for example, metal material can be used to reinforce flexural strength of the mask (300). Additionally, it is preferred that the mask (300) is arranged to contact the upper surface of the fluorescence glass (200) in order to minimize the shadow generated due to the thickness of the slit (310) of the mask (300).

And, a fixing guide (400) having a plurality of insertion coupling holes (410) is coupled in the inside of the case (100). The fixing guide (400) may be formed in a shape of flat plate. The fluorescence glass (200) may be implemented in multiple pieces, each of pieces of the fluorescence glass (200) is insertedly coupled to a respective insertion coupling hole (410) of the fixing guide (400), and the mask (300) is coupled to the fixing guide (400) such that each slit (310) can limit an outside exposure area of each piece of the fluorescence glass (200) to a slit (310) area.

Accordingly, as illustrated in FIG. 2, the fixing guide (400) is safely coupled inside the case (100) to a bottom surface of the lower case (110), the fluorescence glass (200) is insertedly coupled to each of the insertion holes (410) of the fixing guide (400), and in this state, the mask (300) is coupled to the upper side of the fixing guide (400). The mask (300) is positioned so that each of the plurality of the slits (310) can be located on the upper side of the fluorescence glass (200) and the outside exposure area of outside exposure area is limited to the slit (310) area.

One or more guide protrusions (420) are formed at the fixing guide (400) to guide a position which is coupled with the mask (300), and one or more guide holes (320) are formed at the mask (300) to be insertedly coupled with the guide protrusions (420). Therefore, the position of the mask (300) is guided by coupling the guide protrusion (420) and the guide hole (320) to each other so that the mask (300) can be fixed to a precise location, and the slit (310) of the mask (300) is positioned on the upper side of the fluorescence glass (200) and therefore the outside exposure area of the fluorescence glass (200) can be located at the accurate and proper location.

In addition, in a state that the fluorescence glass (200) is insertedly coupled to the insertion coupling hole (410) of the fixation guide (400), as illustrated in FIG. 3(a) the upper surface of the fluorescence glass (200) forms a same plane as an upper surface of the fixing guide (400), and as shown in FIG. 3(b) the mask (300) is coupled to the fixing guide (400) to be contacted with the upper surface of the fixing guide (400) and the upper surface of the fluorescence glass (200).

Like this, the mask (300) with the thin plate shape is arranged to be contacted with the upper surface of the fluorescence glass (200), and therefore the shadow caused by the thickness of the slit (310) can be minimized, the problem of lowering the detection amount of the light by the shadow may be minimized, and the accuracy can be improved.

Additionally, a horizontal guide hole (432) and a vertical guide hole (431) may be formed at one end portion of the fixing guide (400) to guide the safe coupling location of the fixing guide (400) with respect to the case (100), and a horizontal guide protrusion (112) and a vertical guide protrusion (111) are protrudingly formed on the bottom surface of the case (100) to be insertedly interlocked with the horizontal guide hole (432) and the vertical guide hole (431), respectively.

Like this, because the position of the fixing guide (400) also can be guided, the fixing guide (400) can be securely fixed to an accurate location inside the case (100), and the fluorescence glass (200) and the mask (300) coupled with the fixing guide (400) can be fixed to a precise location as well.

And, the slit (310) of the mask (300) and the fluorescence glass (200) can be arrange such that they cross the opening unit (102) of the case (100) in one direction in a state that they are arranged inside the case (100) by the fixing guide (400). As described above, this is for having a line shape like a reaction area of a general specimen strip, and accordingly, if the test light is applied, the fluorescence with a line shape along the slit (310) is generated.

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. A reference cassette for a fluorescence immunoassay diagnostic apparatus which is inserted into the apparatus diagnosing a disease from a biopsy specimen using fluorescence and generates fluorescence by a test light of an optical module, the reference cassette for the fluorescence immunoassay diagnostic apparatus comprising:
  a case configured to be insertable into the fluorescence immunoassay diagnostic apparatus, wherein an opening is formed at at least a part of an upper side of the case so that an inner space of the case is exposed to an outside of the case; and
  a fluorescence glass disposed at the inner space of the case so that the fluorescence glass is exposed to the outside of the case through the opening of the case,
  wherein the fluorescence glass is configured to generate the fluorescence by the test light of the optical module and constantly maintain fluorescence characteristics,
  wherein a mask is disposed on an upper surface of the fluorescence glass inside the case so that an area of the fluorescence glass exposed to the outside of the case is limited to a specific area of the fluorescence glass,
  wherein the mask has one or more slits, and the fluorescence glass is exposed through the slits,
  wherein a separate fixing guide having a plurality of insertion coupling holes is coupled to an inside of the case, the fluorescence glass includes a plurality of pieces of the fluorescence glass, each piece of the fluorescence glass is insertedly coupled to a respective insertion coupling hole of the fixing guide, and the mask is coupled to the fixing guide so that each of the slits limits an outside exposure area of the fluorescence glass to a slit area, and wherein an upper surface of the fluorescence glass and an upper surface of the fixing guide are in a same plane as each other in a state that the fluorescence glass is insertedly coupled to the insertion coupling holes of the fixing guide, and the mask is coupled to the fixing guide to contact the upper surface of the fluorescence glass and the upper surface of the fixing guide.

2. The reference cassette for the fluorescence immunoassay diagnostic apparatus of claim 1, wherein a guide protrusion is formed at the fixing guide to guide a coupling location of the mask, and a guide hole is formed at the mask to be insertedly coupled with the guide protrusion.

3. The reference cassette for the fluorescence immunoassay diagnostic apparatus of claim 1, wherein the slits of the mask and the fluorescence glass cross the opening of the case in one direction in a state that the slits of the mask and the fluorescence glass are arranged inside the case by the fixing guide.

\* \* \* \* \*